United States Patent [19]

Nedelec et al.

[11] Patent Number: 4,503,053
[45] Date of Patent: Mar. 5, 1985

[54] C-HOMO-9-OXA-ERGOLINES

[75] Inventors: Lucien Nedelec, Le Raincy; Jean-Claude Gasc, Bondy; Patrick Fauveau, Livry-Gargan, all of France

[73] Assignee: Roussel Uclaf, Paris, France

[21] Appl. No.: 532,740

[22] Filed: Sep. 15, 1983

[30] Foreign Application Priority Data

Sep. 20, 1982 [FR] France .................. 82 15773

[51] Int. Cl.³ .................. A61K 31/535; C07D 498/06
[52] U.S. Cl. .................. 514/239; 544/99; 546/93; 574/232; 574/233; 574/234; 574/227
[58] Field of Search .................. 544/99; 424/248.52, 424/248.53, 248.54, 248.55, 248.56, 248.57, 248.58

[56] References Cited
U.S. PATENT DOCUMENTS
4,313,944 2/1982 Nedelec et al. .................. 544/99 X Primary Examiner—Richard L. Raymond
Attorney, Agent, or Firm—Charles A. Muserlian

[57] ABSTRACT

Novel C-homo-9-oxa-ergolines of the formula

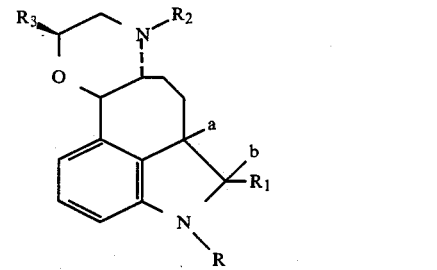

wherein R is selected from the group consisting of hydrogen and alkyl of 1 to 4 carbon atoms, $R_1$ is selected from the group consisting of hydrogen, chlorine and bromine or taken with b forms =O, a and b form a carbon-carbon bond or a is hydrogen when $R_1$ and b form =O, $R_2$ is selected from the group consisting of hydrogen, alkyl of 1 to 4 carbon atoms, aralkyl of 7 to 12 carbon atoms and cycloalkylalkyl of 4 to 7 carbon atoms, $R_3$ is selected from the group consisting of hydroxymethyl, alkylthiomethyl of 1 to 5 alkyl carbon atoms, cyanomethyl, carboxy optionally esterified with an aliphatic alcohol of 1 to 5 carbon atoms and

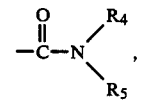

$R_4$ is selected from the group consisting of hydrogen and alkyl of 1 to 4 carbon atoms, $R_5$ is alkyl of 1 to 4 carbon atoms or $R_4$ and $R_5$ taken with the nitrogen atom form a saturated heterocycle optionally containing a second heteroatom having dopaminergic agonist, serotoninergic and antihypertensive activity as well as prolactin secretion inhibition and antianoxic activities and their preparation and intermediates.

35 Claims, No Drawings

C-HOMO-9-OXA-ERGOLINES

STATE OF THE ART

The 9th Edition of Merck Index describes lysergic acid and U.S. Pat. No. 4,318,910 and published European patent application Ser. No. 0033,767 describe indolobenzoxazines. U.S. Pat. Nos. 4,313,944 and 4,355,135 describe a morpholino ring is only substituted on the nitrogen atom. Copending U.S. patent application Ser. No. 493,355 filed May 10, 1983 describes 9-oxalysergic acid derivatives.

OBJECTS OF THE INVENTION

It is an object of the invention to provide the novel compounds of formula I and their non-toxic, pharmaceutically acceptable acid addition salts and their preparation.

It is another object of the invention to provide novel antihypertensive and dopaminergic agonist compositions and a method of treating hypertension and of inducing dopaminergic agonist activity in warm-blooded animals.

It is a further object of the invention to provide novel compositions for treating hypersecretion of prolactin and a method of treating hypersecretion of prolactin in warm-blooded animals.

It is an additional object of the invention to provide compositions for treating cerebral hypoxia and a method of increasing cerebral blood flow in warm-blooded animals.

These and other objects and advantages of the invention will become obvious from the following description.

THE INVENTION

The novel compounds of the invention are selected from the group consisting of C-homo-9-oxa-ergolines of the formula

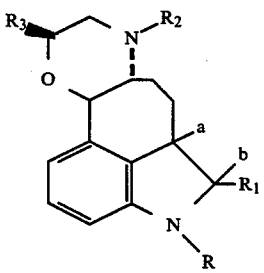

wherein R is selected from the group consisting of hydrogen and alkyl of 1 to 4 carbon atoms, $R_1$ is selected from the group consisting of hydrogen, chlorine and bromine or taken with b forms =O, a and b form a carbon-carbon bond or a is hydrogen when $R_1$ and b form =O, $R_2$ is selected from the group consisting of hydrogen, alkyl of 1 to 4 carbon atoms, aralkyl of 7 to 12 carbon atoms and cycloalkylalkyl of 4 to 7 carbon atoms, $R_3$ is selected from the group consisting of hydroxymethyl, alkylthiomethyl of 1 to 5 alkyl carbon atoms, cyanomethyl, carboxy optionally esterified with an aliphatic alcohol of 1 to 5 carbon atoms and

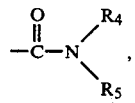

$R_4$ is selected from the group consisting of hydrogen and alkyl of 1 to 4 carbon atoms, $R_5$ is alkyl of 1 to 4 carbon atoms or $R_4$ and $R_5$ taken with the nitrogen atom form a saturated heterocycle optionally containing a second heteroatom and their non-toxic, pharmaceutically acceptable acid addition salts.

Examples of alkyl of 1 to 4 carbon atoms are preferably methyl, ethyl, propyl and isopropyl and examples of AlK is methyl, ethyl, propyl and isopropyl. Examples of aliphatic alcohols of 1 to 5 carbon atoms are methanol, ethanol, propanol and isopropanol. Examples of aralkyl of 7 to 12 carbon atoms are benzyl and phenethyl optionally substituted with at least one member of the group consisting of halogens, methyl, ethyl, methoxy, —OH and —$CF_3$ and cycloalkylalkyl is preferably cyclopropylmethyl. Examples of alkylthiomethyl are n-propylthiomethyl, ethylthiomethyl and especially methylthiomethyl. Examples of heterocycles formed by

are pyrrolidino, piperidino, morpholino or piperazino and the second ring nitrogen atom, if present, may be optionally substituted with alkyl of 1 to 4 carbon atoms.

The dotted line at the junction between the morpholino ring and the benzocycloheptene ring signifies the trans configuration. It is understood that the compounds of the invention may be in racemic form or as optically active isomers.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and aryl carboxylic acids.

Among the preferred compounds of formula I are those wherein a and b form a carbon-carbon bond, those wherein R is hydrogen, those wherein $R_1$ is hydrogen, chlorine or bromine, those wherein $R_2$ is alkyl of 1 to 4 carbon atoms, those wherein $R_3$ is hydroxymethyl, methylthiomethyl, cyanomethyl, —COOH optionally esterified with an aliphatic alcohol of 1 to 4 carbon atoms or

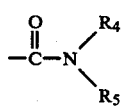

and $R_4$ and $R_5$ are individually alkyl of 1 to 4 carbon atoms and their non-toxic, pharmaceutically acceptable acid addition salts.

Specific preferred compounds are ethyl[5RS(-5α,8β,10β)]6-methyl-C-homo-9-oxa-ergoline-8-carboxylate, methyl[5RS(5α,8β,10β)]6-methyl-C-homo-9-oxa-ergoline-8-carboxylate, [5RS(5α,8β,10β)]6-methyl-C-homo-9-oxa-ergoline-8-methanol, [5RS(5α,8β,10β)]6-methyl-C-homo-9-oxa-ergoline-8-acetonitrile and [5RS(5α,8β,10β)]6-methyl-C-homo-9-oxa-ergoline-8-carboxylic acid and their non-toxic, pharmaceutically acceptable acid addition salts.

The novel process of the invention for the preparation of the compounds of formula I comprises cyclizing a compound of the formula

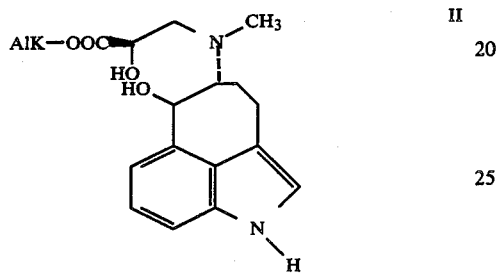
II wherein ALK is alkyl of 1 to 4 carbon atoms to obtain a compound of the formula

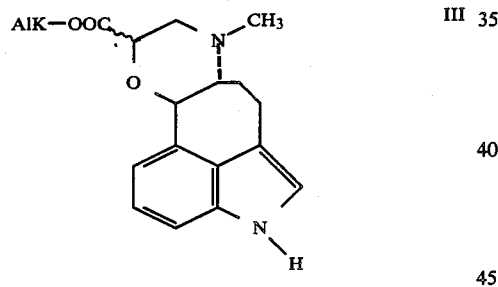
III wherein the wavy line indicates the substituent is in the 8α or 8β-position, isolating the 8β-isomer or epimerizing the 8α-isomer, then esterifying the acid with the 8β-isomeric form to obtain a compound of the formula

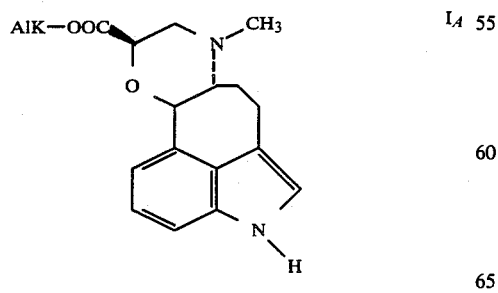
$I_A$ which may be isolated and optionally salified or demethylated to obtain a compound of the formula

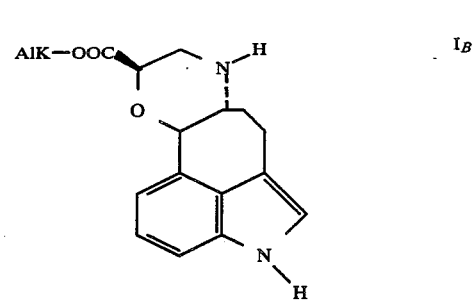
$I_B$ which may be isolated and optionally salified or reacted with an alkylation agent to obtain a compound of the formula

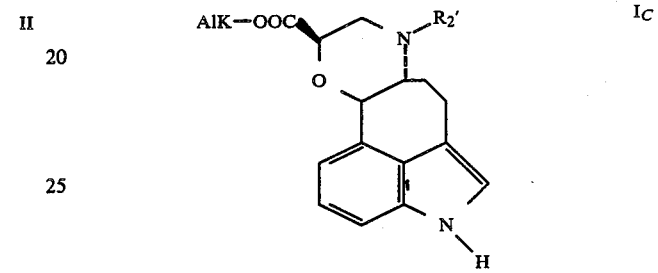
$I_C$ wherein $R_2'$ has the definition of $R_2$ with the exception of hydrogen which may be isolated and optionally salified or reacted with an alkali metal amide and then with an alkyl halide of the formula R'—Hal      IV wherein Hal is chlorine, bromine or iodine and R' is alkyl of 1 to 4 carbon atoms to obtain a compound of the formula

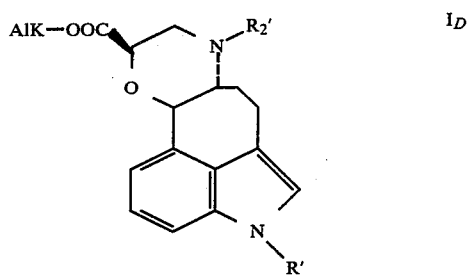
$I_D$ which may be isolated and optionally salified or reacted with a halogenation agent to obtain a compound of the formula

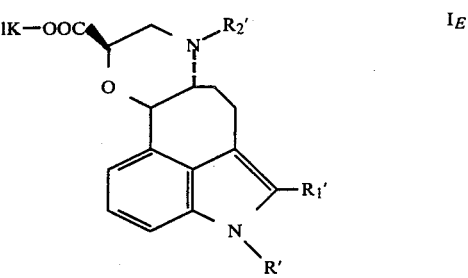
$I_E$ wherein R₁' is chlorine or bromine which may be isolated and optionally salified or reacting the compound of formula I_C with a halogenation agent to obtain a compound of the formula

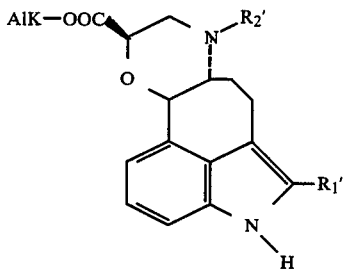   I_F which may be isolated and optionally salified or saponifying a compound of formula I_A to obtain a compound of the formula

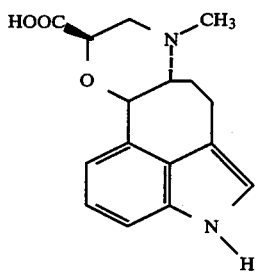   I_G which may be isolated and optionally salified or reacted with an amine of the formula

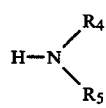   V wherein R₄ and R₅ have the above definition or with a peptide to obtain a compound of the formula

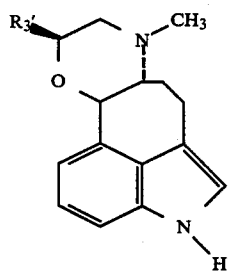   I_H wherein R₃' is

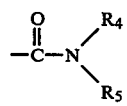

which may be isolated and optionally salified or reducing a compound of formula I_A to obtain a compound of the formula

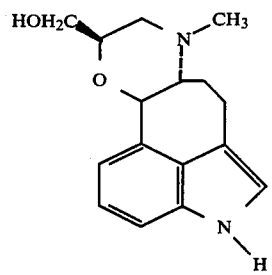   I_I which may be isolated and optionally salified or reacted with methyl chloride or p-toluene sulfonyl chloride to obtain a compound of the formula

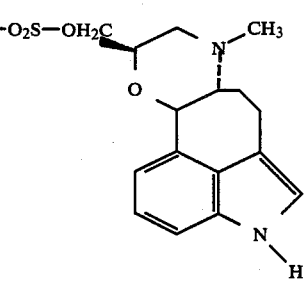   VI wherein K is —CH₃ or p-tolyl and reacting the latter with an alkyl mercaptan or an alkali metal cyanide to obtain a compound of the formula

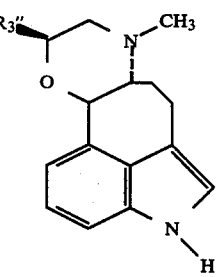   I_J wherein R₃'' is alkylthiomethyl or cyanomethyl which may be isolated and optionally salified or oxidizing a compound of formula I_A to obtain a compound of the formula

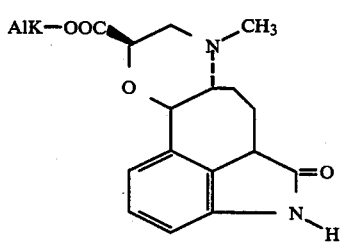   I_K which may be isolated and optionally salified or reducing the latter to obtain a compound of the formula

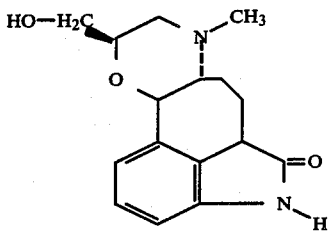

I_L which may be isolated and optionally salified and the compounds of formulae $I_F$, $I_G$, $I_H$, $I_I$, $I_J$, $I_K$ and $I_L$ may be subjected to one of the reactions indicated for the compounds of formula $I_A$ to obtain the corresponding compounds of formula I which may be isolated and optionally salified.

In a preferred mode, the cyclization of the compound of formula II is effected with N-chloro-diisopropylamine in the presence of trisdimethylaminophosphine or hexamethylphosphoramine or with carbon tetrachloride in the presence of triphenylphosphine or trisdimethylaminophosphine then cyclization of the chloro derivative with sodium hydride in a solvent such as dimethoxyethane. The epimerization of the 8α and 8β compounds of formula III is effected by classical methods such as in a basic medium like an alkali metal alcoholate, especially sodium ethylate, at reflux for 1 to 4 hours.

The esterification to obtain the compounds of formula $I_A$ is preferably effected with diazomethane to obtain the methyl ester and the demethylation of the compound of formula $I_A$ is effected by cyanogen bromide followed by reduction with zinc in acetic acid or example. The alkylation of the compound of formula $I_B$ is preferably effected with an alkyl halide, especially an alkyl iodide, in the presence of a condensation agent such as an alkali metal carbonate.

The halide of formula IV may be bromide or chloride but is preferably the iodide and after action in ammonium hydroxide with an alkali metal amide, preferably sodium amide with the compound of formula $I_C$. The halogenation of compounds of formula $I_C$ or $I_D$ is effected with N-chloro-succinimide for chlorination or with a bromine-pyrrolidone complex of the formula

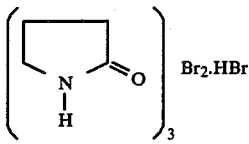

in the case of bromination.

The saponification of compounds of formula $I_A$ is preferably effected with a strong base such as 2N sodium hydroxide or by hydrolysis in an acid media such as reaction with dilute hydrochloric acid in a solvent such as alkanol of 1 to 5 carbon atoms, especially ethanol. The reaction of compounds of formulae $I_G$ and V to obtain a compound of formula $I_H$ is preferably effected by activation of the carboxylic group by formation of a mixed anhydride such as with trifluoroacetic acid or an alkyl haloformate such as isobutyl chloroformate.

The reduction of compounds of formulae $I_A$ or $I_K$ is preferably effected with sodium borohydride in a refluxing solvent such as dioxane alone or with methanol or ethanol or with other reducing agents such as lithium aluminum hydride or sodium cyanoborohydride. The reaction of the compound of formula $I_I$ with methyl chloride or p-toluenesulfonyl chloride is preferably effected in pyridine at room temperature.

The reaction of the compound of formula VI with an alkylmercaptan, preferably methylmercaptan, is effected at room temperature in a solvent such as dimethylacetamide in the presence of sodium hydride. The alkali metal cyanide is preferably sodium or potassium cyanide in a solvent such as dimethylformamide. The oxidation of the compound of formula $I_A$ is preferably effected at room temperature in a mixture of hydrochloric acid and dimethylformamide.

The compounds of formula I except when $R_3$ is —COOH have a basic character and the acid addition salts thereof may be prepared by reacting approximately stoichiometric amounts of the acid and base with or without isolution of the base.

The compounds of formula II may be prepared by reacting a compound of the formula

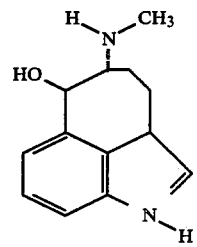

VII with an alkyl glycidate of the formula

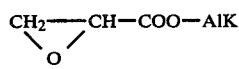

VIII wherein AlK has the above definition. The preferred alkyl glycidate is ethyl glycidate and the reaction is effected at reflux in an alkanol of 1 to 4 carbon atoms, preferably with an alkanol having the same number of carbon atoms as AlK.

The novel antihypertensive, dopaminergic agonist and antianoxic compositions of the invention are comprised of an antihypertensively dopaminergic agonistically and antianoxically effective amount of at least one compound of formula I and their non-toxic, pharmaceutical carrier. The compositions may be in the form of tablets, dragees, gelules, granules, suppositories and injectable solutions or suspensions.

Examples of suitable pharmaceutical carriers are talc, arabic gum, lactose, starch, magnesium stearate, cacao butter, fatty bodies of animal or vegetable origin, aqueous and nonaqueous vehicles, paraffinic derivatives, glycols, diverse wetting agents, dispersants or emulsifiers and preservatives.

The compositions are useful for the treatment of neurological syndromes of extra-pyramidal origin such as for the treatment of Parkinson disease and the treatment of postencephalitic parkinson syndromes. They are also useful for the treatment of prolactin hypersecretion by antehypophysis such as for the treatment of hypogonadism in the male or female. They are also useful for the treatment of cerebral senescence or manifestation of a cerebral hypoxia.

Due to their hypotensive and antihypertensive activity, the compositions are useful for the treatment of essential arterial hypertension, hypertension of the fifties, of menopause, of diabetics, of obesity and of plethoria as well as for the treatment of arterial hypertension due to old age, of artherosclerosis and for the treatment of hypertension of renal origin.

Among the preferred compositions of the invention are those wherein a and b form a carbon-carbon bond, those wherein R is hydrogen, those wherein $R_1$ is hydrogen, chlorine or bromine, those wherein $R_2$ is alkyl of 1 to 4 carbon atoms, those wherein $R_3$ is hydroxymethyl, methylthiomethyl, cyanomethyl, —COOH optionally esterified with an aliphatic alcohol of 1 to 4 carbon atoms or

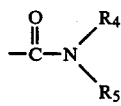

and $R_4$ and $R_5$ are individually alkyl of 1 to 4 carbon atoms and their non-toxic, pharmaceutically acceptable acid addition salts.

Specific preferred compounds are ethyl[5RS(-5α,8β,10β)]6-methyl-C-homo-9-oxa-ergoline-8-carboxylate, methyl[5RS(5α,8β,10β)]6-methyl-C-homo-9-oxa-ergoline-8-carboxylate, [5RS(5α,8β,10β)]6-methyl-C-homo-9-oxa-ergoline-8-methanol, [5RS(5α,8β,10β)]6-methyl-C-homo-9-oxa-ergoline-8-acetonitrile and [5RS(5α,8β,10β)]6-methyl-C-homo-9-oxa-ergoline-8-carboxylic acid and their non-toxic, pharmaceutically acceptable acid addition salts.

The novel method of the invention of inducing antihypertensive dopaminergic agonist and antianoxic activity in warmblooded animals, including humans, comprises administering to animals an amount of at least one compound of formula I and their non-toxic, pharmaceutically acceptable acid addition salts sufficient to cause antihypertensive dopaminergic agonist and antianoxic activity. The compounds may be administered orally, rectally or parenterally and the usual daily dose will vary depending on the condition being treated, the specific compound and the method of administration. The usual daily dose is 0.07 to 2.8 mg/kg of compound of Example 2 for the treatment of Parkinson disease.

The compounds of formula II are novel intermediates and are also an object of the invention.

In the following examples there are described several preferred embodiments to illustrate the invention. However, it should be understood that the invention is not intended to be limited to the specific embodiments.

EXAMPLE 1

Ethyl[5RS(5α,8α,10β)]6-methyl-C-homo-9-oxa-ergoline-8-carboxylate

STEP A: Ethyl 3-[{(5 RS trans)6-hydroxy-3,4,5,6-tetrahydro-1H-cyclohept(c,d)indol-5-yl}methylamino]-2-hydroxy-propanoate A mixture of 32.7 g of RS-trans-5-methylamino-3,4,5,6-tetrahydro-1H-cyclohept(c,d)indol-6-ol [described in French patent No. 2,476,649], 27 g of ethyl glycidate and 600 ml of ethanol was refluxed with stirring under an inert atmosphere for three hours and was then evaporated to dryness. The residue was taken up in methylene chloride and the mixture was extracted five times with 100 ml of 2N hydrochloric acid. The acid fraction was cooled and made alkaline by addition of sodium hydroxide solution. The mixture was extracted with methylene chloride containing 5% of methanol and the organic phase was washed with water, dried and evaporated to dryness under reduced pressure. The residue was taken up in a mixture of ether and methylene chloride and the mixture was allowed to crystallize and was vacuum filtered. The product was washed with ether and dried to obtain 26 g of ethyl 3-[{(5RS trans)6-hydroxy-3,4,5,6-tetrahydro-1H-cyclohept(c,d)indol-5-yl}methylamino]-2-hydroxy-propanoate melting at 130° C.

STEP B: Ethyl[5RS(5α,8β,10β)]6-methyl-C-homo-9-oxaergoline-8-carboxylate 17.2 ml of trisdimethylaminophosphine were added dropwise at −40° C. over 15 minutes to a stirred solution of 13.28 g of the product of Step A, 10.8 g of N-chloro-diisopropylamine and 100 ml of dimethylformamide under an inert atmosphere and the mixture was stirred at −40° C. for 15 minutes and then for two hours without cooling. The mixture was poured into water and was extracted with methylene chloride. The organic phase was dried and evaporated to dryness under reduced pressure. The residue was chromatographed over silica gel and was eluted with a 97-3 methylene chloride-methanol mixture to obtain 700 mg of ethyl[5RS(5α,8α,10β)]6-methyl-C-homo-9-oxa-ergoline-8-carboxylate melting at 148° C., 6 g of ethyl[5RS(-5α,8β,10β)]6-methyl-C-homo-9-oxa-ergoline-8-carboxylate melting at 110° C. and 3.3 g of a mixture of the 8α- and 8β-isomers.

EXAMPLE 2

[5RS(5α,8β,10β)]6-methyl-C-homo-9-oxa-ergoline-8-methanol hydrochloride 5.5 g of sodium borohydride were added under an inert atmosphere with stirring to a solution of 5.5 g of 8β-isomer of Example 1, 100 ml of ethanol and 100 ml of dioxane and the mixture was refluxed for 90 minutes, cooled and poured into water. The mixture was extracted with methylene chloride containing 10% methanol and the organic phase was washed with water, dried and evaporated to dryness under reduced pressure. The residue was empasted with ether and vacuum filtered to obtain 4.10 g of [5RS(5α,8β,10β)]6-methyl-C-homo-9-oxaergoline-8-methanol melting at 255°–260° C.

A mixture of 2.85 g of the said base and 140 ml of methanol was heated to 70° C. and 5 ml of hydrogen chloride in ether were added thereto. The mixture was filtered and the filtrate was allowed to crystallize. The mixture was vacuum filtered and the product was washed and dried to obtain 2.64 g of [5RS(5α,8β,10β)]6-methyl-C-homo-9-oxa-ergoline-3-methanol hydrochloride melting at >250° C. with decomposition.

Analysis: $C_{16}H_{21}ClN_2O_2$: molecular weight=308.80
Calculated: %C 62.23, %H 6.85, %N 9.07, %Cl 11.48.
Found: %C 62.4, %H 6.9, %N 9.1, %Cl 11.6.

EXAMPLE 3

Methyl[5RS(5α,8β,10β)]6-methyl-C-homo-9-oxa-ergoline-8-carboxylate hydrochloride 3.5 g of the mixture of 8α- and 8β-isomers of Example 1 and 50 ml of ethanol were added under an inert atmosphere to a solution of 960 mg of sodium in 50 ml of ethanol and the mixture was refluxed for 4 hours and evaporated to dryness under reduced pressure. The residue was added to water and the cold mixture was neutralized with concentrated hydrochloric acid to obtain the free [5RS(5α,8β,10β)]6-methyl-C-homo-9-oxa-ergoline-8-carboxylic acid.

The said acid was dissolved in 100 ml of methylene chloride and 20 ml of methanol and a solution of 100 ml of diazomethane in methylene chloride was added dropwise thereto at 0° C. The mixture was iced for 48 hours and acetic acid was added to destroy excess diazomethane. The mixture was washed with 2N sodium hydroxide solution, then with water, dried and evaporated to dryness under reduced pressure. The residue was chromatographed over silica gel and was eluted with a 1-1 benzene-ethyl acetate mixture to obtain 1.96 g of methyl [5RS(5α,8β,10β)]6-methyl-C-homo-9-oxa-ergoline-8-carboxylate melting at ≃80° C.

A solution of 1.33 g of the said base in 100 ml of ether was filtered and 4 ml of hydrogen chloride in ether were added thereto. The mixture was allowed to crystallize and was vacuum filtered. The product was washed and dried to obtain 1.25 g of the hylrochloride salt of the base melting at 250° C.

Analysis: $C_{17}H_{20}N_2O_3 \cdot HCl$; molecular weight=336.81. Calculated: %C 60.62, %H 6.28, %N 8.32, %Cl 10.53. Found: %C 60.7, %H 6.3, %N 8.3, %Cl 10.6.

EXAMPLE 4

[5RS(5α,8β,10β)]6-methyl-C-homo-9-oxa-ergoline-8-methylthiomethyl hydrochloride

STEP A: [5RS(5α,8β,10β)]6-methyl-C-homo-9-oxa-ergoline-8-methyl p-toluenesulfonate A solution of 11.7 g of tosyl chloride in 75 ml of pyridine was added dropwise to a solution of 8.4 g of the product of Example 2 in 150 ml of pyridine and the mixture was stirred at room temperature for 16 hours and was poured into water. The mixture was extracted with methylene chloride and the organic phase was washed with aqueous sodium bicarbonate, dried and evaporated to dryness under reduced pressure. The residue was taken up in ether and the mixture was vacuum filtered. The product was washed with ether to obtain 10.7 g of [5RS(5α,8β,10β)]6-methyl-C-homo-9-oxa-ergoline-8-methyl p-toluenesulfonate melting at 152° C.

STEP B: [5RS(5α,8β,10β)]6-methyl-C-homo-9-oxa-ergolinemethylthiomethyl hydrochloride 10 g of a 50% suspension of sodium hydride in vaseline oil were added in small portions at 0° C. to a mixture of 100 ml of anhydrous dimethylacetamide and 50 ml of methylmercaptan and then a solution of 5 g of the product of Step A in 50 ml of dimethylacetamide was added dropwise at room temperature. The mixture was stirred for 2 hours at room temperature and was then poured into a mixture of ice and water. The mixture was extracted with methylene chloride and the organic phase was washed with water, dried and evaporated to dryness under reduced pressure. The residue was chromatographed over silica gel and was eluted with a 7-3 benzene-ethyl acetate mixture to obtain 2.85 g of [5RS(5α,8β,10β)]6-methyl-C-homo-9-oxa-ergolinemethylthiomethyl melting at 158° C.

2.8 g of the said product were dissolved in 100 ml of methanol and the solution was filtered and mixed with 5 ml of hydrogen chloride in methanol. The mixture stood at 0° to 5° C. for one hour and was vacuum filtered. The product was crystallized from methanol to obtain 2.1 g of the hydrochloride of the base melting at 245° C.

EXAMPLE 5

[5RS(5α,8β,10β)]6-methyl-C-homo-9-oxa-ergoline-8-acetonitrile hydrochloride

A solution of 12.75 g of sodium cyanide in 25 ml of water and 50 ml of dimethylformamide was added to a solution of 5.5 g of the product of Step A of Example 4 in 55 ml of dimethylformamide and the mixture was stirred at 60° C. for 16 hours and was cooled. The mixture was poured into water and was extracted with methylene chloride. The organic phase was washed with water, dried and evaporated to dryness under reduced pressure and the residue was empasted with ether and vacuum filtered to obtain 3.3 g of [5RS(5α,8β,10β)]6-methyl-C-homo-9-oxa-ergoline-8-acetonitrile melting at 224° C.

The said base was dissolved in 150 ml of methylene chloride and the solution was filtered and mixed with 5 ml of methanol saturated with hydrogen chloride. The mixture was cooled and vacuum filtered and the product was crystallized from methanol to obtain 3 g of the hydrochloride of the base melting at >250° C.

EXAMPLE 6

[5RS(5α,8β,10β)]6-methyl-C-homo-9-oxa-ergoline-8-N,N-diethylcarboxamide hydrochloride 3.2 ml of tributylene and 1.7 ml of isobutyl chloroformate were added at 10° C. to a mixture of 3.1 g of the acid of Example 3, 80 ml of anhydrous dimethylformamide and 80 ml of anhydrous dioxane and the mixture was stirred at room temperature for one hour and was poured all at once into 50 ml of dioxane and 8 ml of diethylamine. The mixture was stirred for one hour at room temperature and was poured into water. The mixture was extracted with methylene chloride and the organic pace was washed with water, dried and evaporated to dryness under reduced pressure. The residue was taken up in ether to obtain 2.33 g of [5RS(5α,8β,10β)]6-methyl-C-homo-9-oxa-ergoline-8-N,N-diethylcarboxamide melting at 178°-180° C. The mother liquors were passed through silica gel and elution with a 95-5 methylene chloride-methanol yielded another 0.4 g of product melting at 180° C.

A solution of 2.7 g of the said base in 50 ml of methanol was mixed with 3 ml of 3 or 4N hydrogen chloride in ether and crystallization was effected at room temperature. The mixture was vacuum filtered and the product was crystallized from methanol to obtain 2.35 g of the hydrochloride of the base melting at ≃245°-250° C.

EXAMPLE 7

Ethyl[5RS(5α,8β,10β)]2-bromo-6-methyl-C-homo-9-oxa-ergoline-8-carboxylate hydrochloride 9 g of the product of Example 1 were added over 5 minutes to a solution of 18.72 g of pyrrolidone hydrotribromide in 2.4 liters of dioxane at room temperature and the dioxane was evaporated. The residue was taken up in a saturated sodium carbonate solution and ethyl acetate with stirring and the decanted organic phase was washed with aqueous saturated sodium chloride solution, dried and evaporated to dryness under reduced pressure. The residue was chromatographed over silica gel and was eluted with a 1-1 cyclohexane-ethyl acetate mixture to obtain 6.78 g of product melting at 160° C.

4.5 g of the said product were dissolved at room temperature in 90 ml of methanol and 45 ml of dioxane and 4.5 g of sodium borohydride were added thereto. The mixture was refluxed for one hour and was cooled to room temperature. 100 ml of water were added thereto and the mixture was stirred for 30 minutes and was filtered. The product was rinsed with water to obtain 3.5 g of ethyl[5RS(5α,8β,10β)]2-bromo-6-methyl-C-homo-9-oxa-ergoline-8-carboxylate melting at >260° C.

3 g of the product were suspended in 40 ml of methanol and hydrogen chloride in ether was added dropwise at 0° to 5° C. until the pH was 1. The mixture was stirred for two hours at room temperature and was filtered and the product was rinsed with ether to obtain 3.4 g of the corresponding hydrochloride melting at 255° C.

EXAMPLE 8

[5RS(5α,8β,10β)]2,3-dihydro-2-oxo-6-methyl-C-homo-9-oxa-ergolin-8-methanol hydrochloride STEP A: Ethyl[5RS(5α,8β,10β)]2,3-dihydro-2-oxo-6-methyl-C-homo-9-oxa-ergoline-8-carboxylate 90 ml of concentrated hydrochloric acid were added with stirring to 45 ml of dimethylsulfoxide while keeping the temperature below 20° C. and then 9 g of ethyl[5RS(5α,8β,10β)]6-methyl-C-homo-9-oxa-ergoline-8-carboxylate were rapidly added thereto. The mixture was stirred at room temperature for 30 minutes, was cooled to 0° to 5° C. and neutralized with triethylamine. The mixture was vacuum filtered and the recovered crystals were dissolved in methylene chloride containing 10% methanol. The mixture was evaporated to dryness to obtain 3.1 g of ethyl[5RS(5α,8β,10β)]2,3-dihydro-2-oxo-6-methyl-C-homo-9-oxa-ergoline-8-carboxylate melting at 264° C.

STEP B: [5RS(5α,8β,10β)]2,3-dihydro-2-oxo-6-methyl-C-homo-9-oxa-ergoline-8-methanol hydrochloride 3.1 g of the product of Step A were dissolved at room temperature in 30 ml of ethanol and 10 ml of dioxane and 3.1 g of borohydride were added thereto in small portions. The mixture was refluxed for 2 hours and cooled to room temperature and poured into ice. The mixture was saturated with sodium carbonate and was extracted with methylene chloride. The organic phase was washed with aqueous saturated sodium chloride solution, dried and evaporated to dryness to obtain 1.96 g of [5RS(5α,8β,10β)]2,3-dihydro-2-oxo-6p-methyl-C-homo-9-oxa-ergoline-8-methanol melting at 220° C.

A suspension of 1.85 g of the said compound in 10 ml of methanol was cooled to 0° C. and hydrogen chloride in ether was added thereto until the pH was one. The mixture was stirred at room temperature for 30 minutes and was filtered to obtain 1.74 g of the hydrochloride of the said compound melting at 260° C.

EXAMPLE 9

Tablets were prepared containing 10 mg of [RS(5α,8β,10β)]6-methyl-C-homo-9-oxa-ergoline-8-methanol hydrochloride and sufficient excipient of lactose, starch, talc and magnesium stearate for a final weight of 100 mg.

PHARMACOLOGICAL DATA

A. Rotation behavior after unilateral injury of nigrostriatal bundle

The unilateral lesion was effected with male rats weighing about 220 g by unilateral injection into nigrostriatal dopamingeric bundle of 8 μg of 6-hydroxydopamine in a solution of 2 μg per μl by the method of Ungerstedt [Acta. Physiol. Scand., Vol. 82 (1971), supp. 367, p. 69–93]. In the animals, the direct dopaminergic agonists such as apomorphone administered generally induces a rotating behavior in the contralateral direction to the injured side. The test compounds were administered more than 5 weeks after the lesion and the rats were placed in an automatic rotometer which determined the number of rotations effected by each animal in 2 directions. The compound of Example 2 administered intraperitoneally provoked contralateral rotations at a dose of 0.5 mg/kg.

B. Hypotensive Activity

The hypotensive activity was studied on male rats of the Wistar strain weighing about 300 g and anesthesized with nembutal (50 mg/kg-intravenously). The test compound was administered intravenously through the jugular vein and carotidine arterial pressure was measured before and after the test product administration. The arterial pressure differences were calculated as in Table I and the results are reported in Table I.

TABLE I

| Product of Example | Dose in mg/kg | % Arterial Pressure variation after minutes | | | |
|---|---|---|---|---|---|
| | | 1 | 5 | 10 | 30 |
| 2 | 10 | −44 | −40 | −37 | −31 |
| | 1 | −29 | −25 | −20 | −11 |

C. Acute toxicity

The DL$_0$ lethal dose or that dose which did not cause any deaths after 8 days was determined on mice by intra-eritoneal administration of the compound. The DL$_0$ for the compound of Example 2 was 100 mg/kg.

Various modifications of the products and method of the invention may be made without departing from the spirit or scope thereof and it should be understood that the invention is intended to be limited only as defined in the appended claims.

What we claim is:

1. A compound selected from the group consisting of C-homo-9-oxa-ergolines of the formula

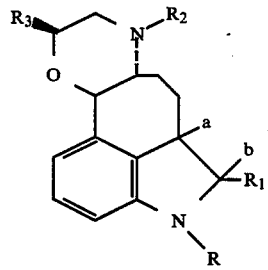

wherein R is selected from the group consisting of hydrogen and alkyl of 1 to 4 carbon atoms, R$_1$ is selected from the group consisting of hydrogen, chlorine and bromine or taken with b forms=0, a and b form a carbon-carbon bond or a is hydrogen when R$_1$ and b form=0, R$_2$ is selected from the group consisting of hydrogen, alkyl of 1 to 4 carbon atoms, aralkyl of 7 to 12 carbon atoms and cycloalkylalkyl of 4 to 7 carbon atoms, R$_3$ is selected from the group consisting of hydroxymethyl, alkylthiomethyl of 1 to 5 alkyl carbon atoms, cyanomethyl, carboxy optionally esterified with an aliphatic alcohol of 1 to 5 carbon atoms and

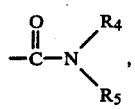

R$_4$ is selected from the group consisting of hydrogen and alkyl of 1 to 4 carbon atoms, R$_5$ is alkyl of 1 to 4 carbon atoms or R$_4$ and R$_5$ taken with the nitrogen atom form a saturated heterocycle optionally containing a second heteroatom.

2. A compound of claim 1 wherein a and b form a carbon-carbon bond.

3. A compound of claim 1 wherein R is hydrogen.

4. A compound of claim 3 wherein R$_1$ is hydrogen, chlorine or bromine, R$_2$ is alkyl of 1 to 4 carbon atoms, R$_3$ is selected from the group consisting of hydroxymethyl, methylthiomethyl, cyanomethyl, —COOH optionally esterified with alkanol of 1 to 4 carbon atoms and

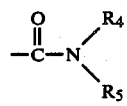

and R$_4$ and R$_5$ are individually alkyl of 1 to 4 carbon atoms.

5. A compound of claim 1 selected from the group consisting of ethyl[5RS(5α,8β,10β)]6-methyl-C-homo-9-oxa-ergoline-8-carboxylate and its non-toxic, pharmaceutically acceptable acid addition salts.

6. A compound of claim 1 selected from the group consisting of methyl[5RS(5α,8β,10β)]6-methyl-C-homo-9-oxa-ergoline-8-carboxylate and its non-toxic, pharmaceutically acceptable acid addition salts.

7. A compound of claim 1 selected from the group consisting of [5RS(5α,8β,10β)]6-methyl-C-homo-9-oxa-ergoline-8-methanol and its non-toxic, pharmaceutically acceptable acid addition salts.

8. An antihypertensive and dopaminergic agonist composition comprising an antihypertensively and dopaminergic agonistically effective amount of at least one compound of claim 1 and an inert carrier.

9. A composition of claim 8 wherein a and b form a carbon-carbon bond.

10. A composition of claim 8 wherein R is hydrogen.

11. A composition of claim 10 wherein R$_1$ is hydrogen, chlorine or bromine, R$_2$ is alkyl of 1 to 4 carbon atoms, R$_3$ is selected from the group consisting of hydroxymethyl, methylthiomethyl, cyanomethyl, —COOH optionally esterified with alkanol of 1 to 4 carbon atoms and

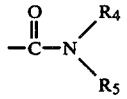

and R$_4$ and R$_5$ are individually alkyl of 1 to 4 carbon atoms.

12. A composition of claim 8 wherein the compound is selected from the group consisting of ethyl[5RS(-5α,8β,10β)]6-methyl-C-homo-9-oxa-ergoline-8-carboxylate and its non-toxic, pharmaceutically acceptable acid addition salts.

13. A composition of claim 8 wherein the compound is selected from the group consisting of methyl[5RS(-5α,8β,10β)]6-methyl-C-homo-9-oxa-ergoline-8-carboxylate and its non-toxic, pharmaceutically acceptable acid addition salts.

14. A composition of claim 8 wherein the compound is selected from the group consisting of [5RS(5α,8β,10β)]6-methyl-C-homo-9-oxa-ergoline-8-methanol and its non-toxic, pharmaceutically acceptable acid addition salts.

15. A method of inducing antihypertensive and dopaminergic agonist activity in warm-blooded animals comprising administering to warm-blooded animals an amount of at least one compound of claim 1 sufficient to cause antihypertensive and dopaminergic agonist activity.

16. A method of claim 15 wherein a and b form a carbon-carbon bond.

17. A method of claim 15 wherein R is hydrogen.

18. A method of claim 15 wherein R$_1$ is hydrogen, chlorine or bromine, R$_2$ is alkyl of 1 to 4 carbon atoms, R$_3$ is selected from the group consisting of hydroxymethyl, methylthiomethyl, cyanomethyl, —COOH optionally esterified with alkanol of 1 to 4 carbon atoms and

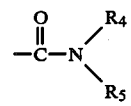

and R$_4$ and R$_5$ are individually alkyl of 1 to 4 carbon atoms.

19. A method of claim 15 wherein the compound is selected from the group consisting of ethyl[5RS(-5α,8β,10β)]6-methyl-C-homo-9-oxa-ergoline-8-carboxylate and its non-toxic, pharmaceutically acceptable acid addition salts.

20. A method of claim 15 wherein the compound is selected from the group consisting of methyl[5RS(-5α,8β,10β)]6-methyl-C-homo-9-oxa-ergoline-8-carboxylate and its non-toxic, pharmaceutically acceptable acid addition salts.

21. A method of claim 15 wherein the compound is selected from the group consisting of [5RS(5α,8β,10β)]6-methyl-C-homo-9-oxa-ergoline-8-methanol and its non-toxic, pharmaceutically acceptable acid addition salts.

22. A method of treating hypersecretion of prolactin in warm-blooded animals comprising administering to warm-blooded animals an amount of at least one compound of claim 1 sufficient to prevent hypersecretion of prolactin.

23. A method of claim 22 wherein a and b form a carbon-carbon bond.

24. A method of claim 22 wherein R is hydrogen.

25. A method of claim 24 wherein R$_1$ is hydrogen, chlorine or bromine, R$_2$ is alkyl of 1 to 4 carbon atoms, R$_3$ is selected from the group consisting of hydroxymethyl, methylthiomethyl, cyanomethyl, —COOH optionally esterified with alkanol of 1 to 4 carbon atoms and

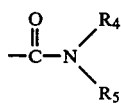

and R4 and R5 are individually alkyl of 1 to 4 carbon atoms.

26. A method of claim 24 wherein the compound is selected from the group consisting of ethyl[5RS(-5α,8β,10β)]6-methyl-C-homo-9-oxa-ergoline-8-carboxylate and its non-toxic, pharmaceutically acceptable acid addition salts.

27. A method of claim 24 wherein the compound is selected from the group consisting of methyl[5RS(-5α,8β,10β)]6-methyl-C-homo-9-oxa-ergoline-8-carboxylate and its non-toxic, pharmaceutically acceptable acid addition salts.

28. A method of claim 24 wherein the compound is selected from the group consisting of [5RS(5α,8β,10β)]6-methyl-C-homo-9-oxa-ergoline-8-methanol and its non-toxic, pharmaceutically acceptable acid addition salts.

29. A method of treating cerebral hypoxia in warm-blooded animals comprising administering to warm-blooded animals an amount of at least one compound of claim 1 sufficient to treat cerebral hypoxia.

30. A method of claim 29 wherein a and b form a carbon-carbon bond.

31. A method of claim 29 wherein R is hydrogen.

32. A method of claim 29 wherein R₁ is hydrogen, chlorine or bromine, R₂ is alkyl of 1 to 4 carbon atoms, R₃ is selected from the group consisting of hydroxymethyl, methylthiomethyl, cyanomethyl, —COOH optionally esterified with alkanol of 1 to 4 carbon atoms and

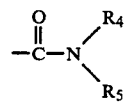

and R4 and R5 are individually alkyl of 1 to 4 carbon atoms.

33. A method of claim 29 wherein the compound is selected from the group consisting of ethyl[5RS(-5α,8β,10β)]6-methyl-C-homo-9-oxa-ergoline-8-carboxylate and its non-toxic, pharmaceutically acceptable acid addition salts.

34. A method of claim 29 wherein the compound is selected from the group consisting of methyl[5RS(-5α,8β,10β)]6-methyl-C-homo-9-oxa-ergoline-8-carboxylate and its non-toxic, pharmaceutically acceptable acid addition salts.

35. A method of claim 29 wherein the compound is selected from the group consisting of [5RS(5α,8β,10β)]6-methyl-C-homo-9-oxa-ergoline-8-methanol and its non-toxic, pharmaceutically acceptable acid addition salts.

* * * * *